3 Sheets—Sheet 1.

F. WOLLE.

MACHINE FOR MAKING PAPER BAGS.

No. 796. Reissued Aug. 16, 1859.

THE NORRIS PETERS CO., PHOTO-LITHO., WASHINGTON, D. C.

F. WOLLE.

MACHINE FOR MAKING PAPER BAGS.

No. 796. Reissued Aug. 16, 1859.

THE NORRIS PETERS CO., PHOTO-LITHO., WASHINGTON, D. C.

F. WOLLE.

MACHINE FOR MAKING PAPER BAGS.

No. 796. Reissued Aug. 16, 1859.

THE NORRIS PETERS CO., PHOTO-LITHO., WASHINGTON, D. C.

UNITED STATES PATENT OFFICE.

FRANCIS WOLLE, OF BETHLEHEM, PENNSYLVANIA.

IMPROVEMENT IN MACHINES FOR MAKING PAPER BAGS.

Specification forming part of Letters Patent No. 20,838, dated July 6, 1858; Reissue No. 796, dated August 16, 1859.

*To all whom it may concern:*

Be it known that I, FRANCIS WOLLE, of the borough of Bethlehem, in the county of Northampton and State of Pennsylvania, have invented new and useful improvements to be applied to machinery for making bags of paper or other suitable material, to facilitate the economical and rapid working thereof; and I do declare that the following is a full, clear, and exact description of the construction and operation of the same.

My invention consists, first, in a novel mode of combining and arranging a system of creasing and lapping mechanism for forming the bottom lap or seam of the bag, whereby I prevent the loss of the strips of paper usually cut off to make the bottom seam or lap of the bag.

It consists, secondly, in the forming of a lap in the manufacture of a bag of paper or other material by the combination of a creasing-blade with two rolling-surfaces without the aid of any stationary edges or other contrivances.

It consists, thirdly, in a certain mode of applying the revolving lapper-shaft, in combination with the creaser and the apparatus for feeding the bags to the action of the creaser and lapper-shaft.

The accompanying drawings, making part of this specification, represent the parts embracing all the features of my new invention.

Figure 3:
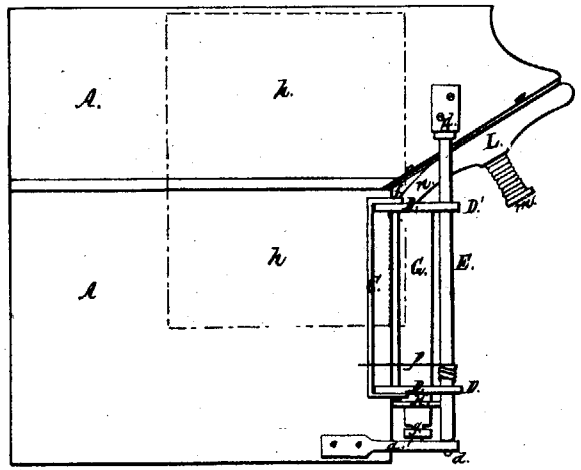
Figure 4:
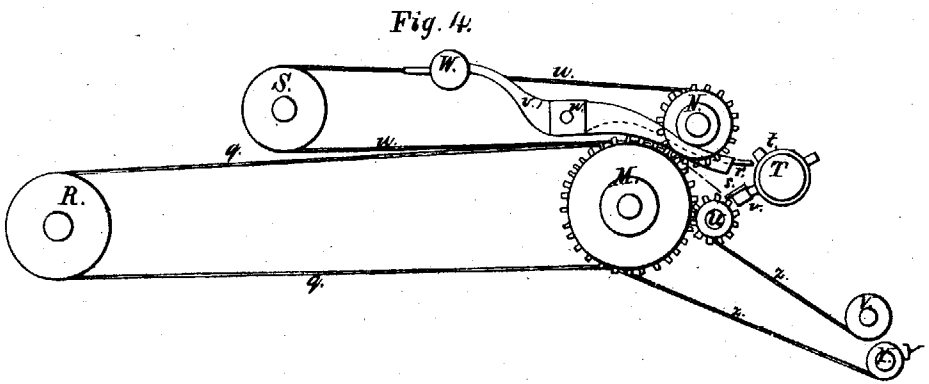
Figure 1:
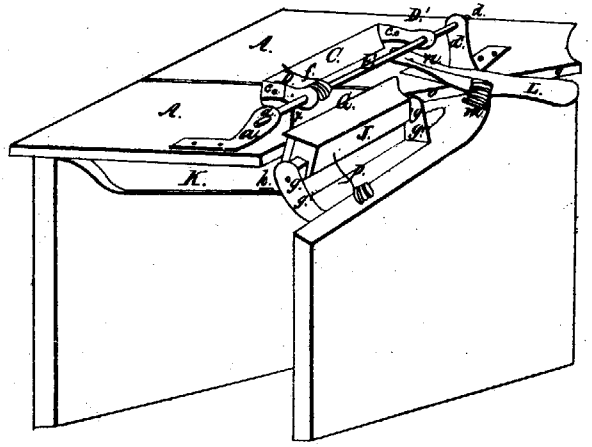
Figure 2:
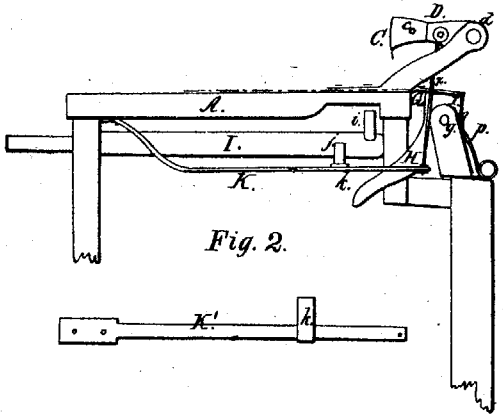
Figure 8:
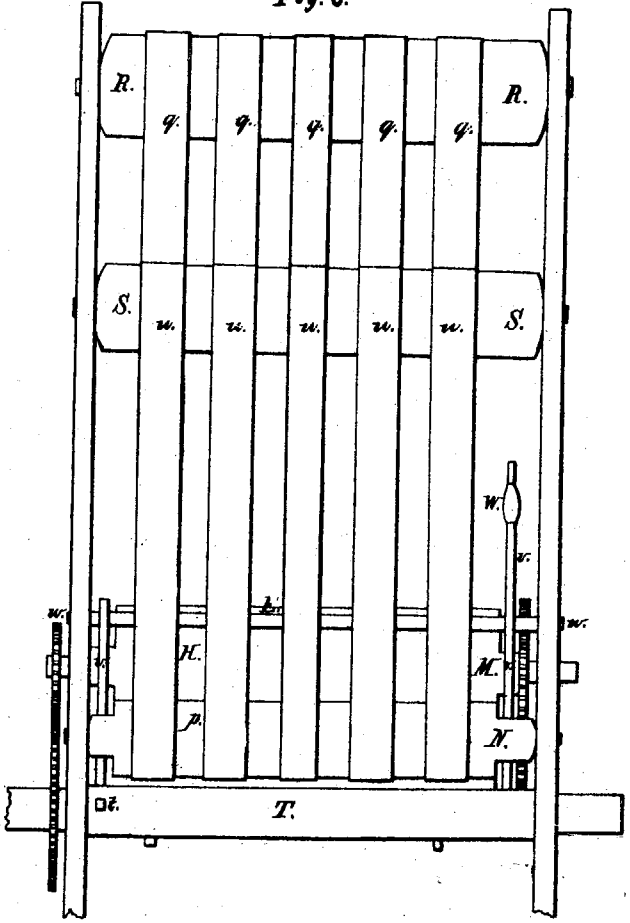
Figure 5:
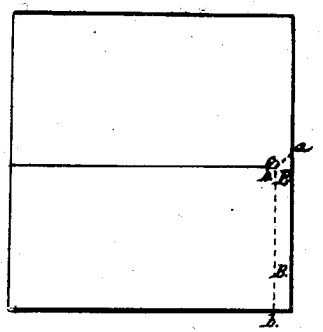
Figure 6:
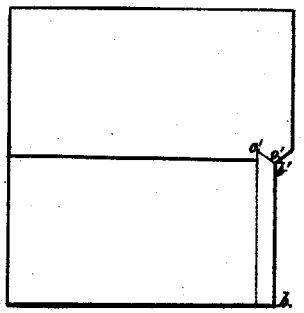
Figure 9:
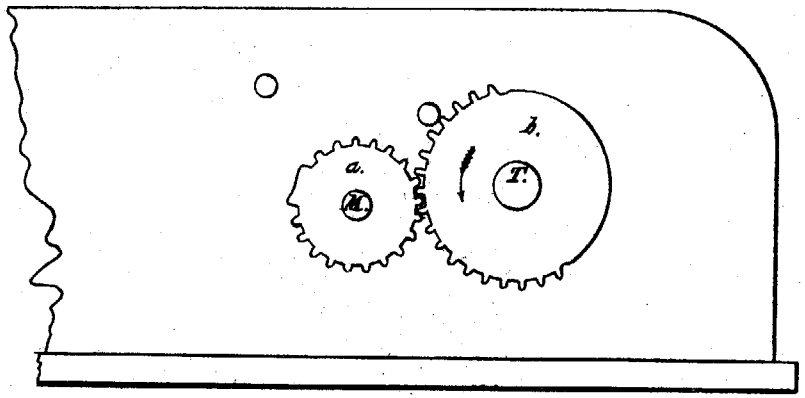
Figure 7:
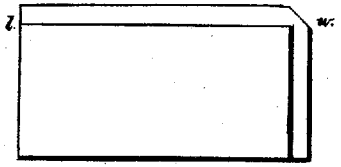

Figure 1 is a perspective view of the lapping apparatus. Fig. 2 is a sectional view of the lapping apparatus. Fig. 3 is a top view of the same, showing in red outline the position of the paper to be cut and lapped. Fig. 4 is a sectional view of the revolving shaft used in lapping the side of the bag and the parts connected therewith. Fig. 5 exhibits the shape of the paper to be made into a bag and the part to be lapped over. Fig. 6 exhibits the edge lapped over. Fig. 7 exhibits the paper folded ready for pasting and lapping. Fig. 8 is a plan of the parts connected with the revolving shaft for lapping the side of the bag. Fig. 9, Sheet II, shows the gear-connection of the driving-shaft and the feed-roller M.

In Figs. 1, 2, and 3, *a a* represent a table or inclined plane, upon which the paper to be made into a bag is placed.

The feeding of the paper may be done by hand or by additional machinery, as described in the specification of a patent granted to me the 29th day of May, 1855.

In preparing a piece of paper for making a bag it is usual to cut off part of one edge, as B B, Fig. 5, so that the remaining part of the same edge can, when the piece is doubled, as Fig. 7, be lapped over it to make the joint or seam in the bottom of the bag. Instead of cutting off this part of the edge, B B, Fig. 5, I lap it over, as shown in Fig. 6, so that when the piece is doubled, as Fig. 7, the strip B B, Fig. 5, comes between the two sides of the bag. This is performed by what I call a "lapping apparatus," consisting of three principal parts, the shear, the creaser, and the lapper. The shear is a metal blade, L, which hangs on a fulcrum-pin, *m*, Figs. 1 and 3.

O is a fixed strip of steel, standing out at an obtuse angle from the lower part of the table, and against which the shear-blade cuts.

The shear may be entirely of steel, or be made of wood or iron, with a strip of steel attached to it. It has an arm, *n*, made to extend under one arm, D′, of the creaser-frame. Around the fulcrum-pin *m* of the shear there is a coiled spring to raise and to hold up the point of the shear-blade.

The creaser consists of the following parts: C, Figs. 1, 2, and 3, is a dull-edged metal blade with a flange, *e e*, at each end set at right angles. This blade is movable on pins *c c*, running through the flanges *e e* and the two arms, D D′, of the rock-shaft E, hung on the centers *d d* and working in two bearings, *d′ d′*. The blade C is held in its proper position by a spring, *f*, pressing on its upper edge. It is connected by the rod *x* to the spring *k* under the table *a a*. The lapper consists of a square shaft, T, swinging on the centers *g g* in the bearings *g′ g′*, with a metal blade, G, attached to the top of the shaft T and projecting over it on the side toward the table. H is an arm fixed to one end of the square shaft F.

I is a revolving shaft supported in bearings in the framing with two cams, *i* and *j*.

K is a spring attached at one end to the bottom of the table *a*, with an arm, *k*, projecting under the shaft I. This spring K is represented under Fig. 2 detached from the table to show the projecting arm *k*.

The paper being placed on the inclined plane or table *a a*, Fig. 3, as represented in red outline, part of one edge of the paper being under the shear-blade L, under the creaser-blade C, and on the lapper-edge G, the shaft I, Fig. 2, being made to revolve by gear-connection with other parts of the machinery, or independently thereof, the cam *j* will bear down on the spring by passing the arm *k*. The one end of the spring K being connected with the creaser-arm D by the rod *x*, the blade C is brought down so that the lower edge will press upon the paper near the edge of the table in the direction of the line dotted with red, (Fig. 3,) the shear-blade being so constructed with an arm, *n*, that the movement of the arm D′ of the creaser-shaft will operate upon it when forced down. This will cause the shear to make a diagonal slit, *a a*, Fig. 5, in the direction of the steel blade *o o*, Fig. 3, against which it cuts. While the creaser-blade C is held down during the time the cam *j* is passing over the length of the arm *k*, the other cam, *i*, operates upon the arm H by forcing it back. This brings the projection G of the shaft F against the creaser-blade C, thus turning over the edge of the paper. The creaser-blade being held merely by the spring *f*, it will yield to the pressure of the projection G and escape from its grasp at the moment it bears hard upon the edge of the table, and so complete the lap, as represented by Fig. 6. The cams having passed the arm *k* of the spring K and the arm H of the upper shaft, F, the creaser is raised by the spring K and the lapper brought to its former open position by the spring *p*. This operation being completed, the paper is folded into shape, as exhibited by Fig. 7, ready for pasting and lapping.

Next I describe the revolving shaft for lapping the side of the bag.

Fig. 4 is a sectional view, and Fig. 8 a plan, of this improvement. U is the revolving lapper-shaft consisting of a small roller geared by a spur-wheel to the feed-roller M. T is the driving-shaft, revolving in the direction of the arrow, Fig. 9, Sheet 2. *q g* and *u u* are two aprons consisting of tapes running round the rollers R M and S N, with journals working in bearings in the sides of the framing. The roller M receives an intermittent rotary motion by means of a spur-wheel on one end of it, *a*, Fig. 9, Sheet 2, which gears another spur-wheel, *b*, Fig. 9, on the driving-shaft, which has teeth on a part only of its circumference. This causes the apron to receive one motion for every revolution of the driving-shaft and then to become stationary for a time.

Referring to Figs. 4 and 8, S is the creaser-blade attached to two arms, *v v*, of a rock-shaft, *w*. *r* is another arm of the shaft, with a poise, W. V Y are two rollers with journals running in bearings in the framing. An endless apron consisting of tapes *z z*, runs round the rollers M Y, which receives the bags and delivers them when finished for drying. *t* is a stud on the driving shaft. We suppose the paper, cut, lapped, and folded to the condition shown in Fig. 7, placed upon the apron over the roller R. One of the movements of the aprons will serve to carry the folded paper forward toward the driving-shaft T so far that it will have the edge intended for the lap of the side of the bag upon the lapper-roller U, as represented in the red outline, Fig. 4. While in this position we suppose it to be pasted by means of proper mechanism, and immediately as this is done the shaft T, revolving in the direction of the arrow, the stud *t* operates upon the arm *r* of the creaser and brings down the blade S upon the paper in the line *l w*, Fig. 7, where the lapping commences, which is closed to the edge of the upper side of the bag and forces it down between the converging surfaces of the rollers M U. The rollers, having an intermittent motion, now revolve, the aprons are set in motion, and the paper is carried down between the rollers, which, being set close together, finish the lap commenced by the entry of the creaser-blade *s* between the converging surfaces of the rollers M U. The creaser-blade *s* is raised as soon as detached from the stud *t* by the poise W, attached to an arm, *v′*, of the creaser-shaft.

I wish to be distinctly understood that the formation of the lap, as just above described, is entirely effected by means of the creaser-blade *s* and the rollers M U, and that the duty of the apron *q q* is merely to convey the bag to the said rollers, and that of the apron Z, merely to convey it away from the said rollers. The bag having passed between the rollers M U and been delivered upon the apron Z, passes under the roller V, where it receives another slight pressure, preparatory to its being dried.

I am aware that rollers have been employed previous to the date of this invention for finishing the laps of paper bags after the said bags have been folded by the operation of creaser-blades, in combination with other devices intervening between the said blades and the rollers. In such cases, however, the rollers had nothing to do with the actual folding of the lap, and I do not claim the use of rollers when not constituting an essential part of the folding device; but

What I claim as my invention is—

1. The combination of the creaser C and lappers F G, arranged and operating substantially in the manner and for the purpose herein described and set forth.

2. The folding of a lap in the manufacture of a bag of paper or other material by means of a creaser-blade and two rolling-surfaces operating in combination with each other, substantially as herein described.

3. The revolving lapper-shaft, U in combination with the creaser *v s*, the feed-roller M, and aprons *u q*, substantially as herein described, the creaser being brought into operation on the lap during the intermission in the motion of the feed rollers.

FRANCIS WOLLE.

Witnesses:
JAMES H. WOLLE,
JOHN F. WOLLE.